(12) United States Patent
Li

(10) Patent No.: US 12,220,428 B2
(45) Date of Patent: Feb. 11, 2025

(54) ETHANOL HARDENER AND USE THEREOF

(71) Applicant: Xueyi Li, Beilin District Xi'an (CN)

(72) Inventor: Xueyi Li, Beilin District Xi'an (CN)

(*) Notice: Subject to any disclaimer, the term of this patent is extended or adjusted under 35 U.S.C. 154(b) by 558 days.

(21) Appl. No.: 17/607,053

(22) PCT Filed: Apr. 29, 2020

(86) PCT No.: PCT/CN2020/087705
§ 371 (c)(1),
(2) Date: Oct. 28, 2021

(87) PCT Pub. No.: WO2020/221283
PCT Pub. Date: Nov. 5, 2020

(65) Prior Publication Data
US 2022/0226369 A1 Jul. 21, 2022

(30) Foreign Application Priority Data
Apr. 29, 2019 (CN) .................. 201910355441.6

(51) Int. Cl.
*A61K 33/18* (2006.01)
*A61K 9/00* (2006.01)
*A61K 9/08* (2006.01)
*A61K 31/045* (2006.01)
*A61K 31/167* (2006.01)
*A61K 49/04* (2006.01)
*A61P 9/14* (2006.01)

(52) U.S. Cl.
CPC ............ *A61K 33/18* (2013.01); *A61K 9/0019* (2013.01); *A61K 9/08* (2013.01); *A61K 31/045* (2013.01); *A61K 31/167* (2013.01); *A61P 9/14* (2018.01); *A61K 49/04* (2013.01)

(58) Field of Classification Search
None
See application file for complete search history.

(56) References Cited

U.S. PATENT DOCUMENTS

| | | | | | |
|---|---|---|---|---|---|
| 6,160,025 | A | * | 12/2000 | Slaikeu | A61L 24/06 514/772.1 |
| 2008/0050436 | A1 | | 2/2008 | Chu | |
| 2015/0272666 | A1 | * | 10/2015 | Wang | A61P 9/12 424/9.4 |

FOREIGN PATENT DOCUMENTS

| | | |
|---|---|---|
| CN | 1465348 A | 1/2004 |
| CN | 1665545 A | 9/2005 |
| CN | 105263431 A | 1/2016 |
| CN | 111840265 A | 10/2020 |

OTHER PUBLICATIONS

English translation for CN 1465348A (Year: 2004).*
Product Information sheet for Ultravist dated Aug. 29, 2013 and obtained from the website: https://resources.bayer.com.au/resources/uploads/Pl/file9435.pdf (Year: 2013).*
Widipedia article on "iopromide" obtained from the website https://en.wikipedia.org/wiki/Iopromide (date unknown).*
Dec. 5, 2022 Chinese First Office Action issued in Chinese Patent Application No. 2019103554416.
International Search Report dated Jul. 29, 2020 issued in PCT application No. PCT/CN/2020087705.
Written Opinion of the International Search Authority dated Jul. 29, 2020 issued in PCT application No. PCT/CN/2020087705.
Haines David E., "Intracoronary Ethanol Ablation in Swine Characterization of Myocardial Injury in Target and Remote Vascular Beds," Journal of Cardiovascular Electrophysiology, vol. 5, issue 1, Jan. 31, 1994, p. 41 to 49.
Toru Saguchi et al. "Guidelines for Absolute Ethanol for Use in Vascular Embolization, 2016 edition" Interventional Radiology, vol. 3, Issue 1, Dec. 31, 2018, p. 44-45.
Haibo Li,. "Clinical Study of Lower Limb Venous Malformation in Children with Ethanol Sclerotherapy," Modern Hospital, vol. 12, Jul. 31, 2012. p. 32-33, right column "1.2 Method".

* cited by examiner

*Primary Examiner* — Sin J Lee
(74) *Attorney, Agent, or Firm* — Harness, Dickey & Pierce, P.L.C.

(57) ABSTRACT

Disclosed are an ethanol hardener and the use thereof. The ethanol hardener contains ethanol, a water-soluble iodine preparation and water, wherein the volume percent of the ethanol is 76-98%, and the mass-volume ratio of the iodine element in the water-soluble iodine preparation to the iodine containing composition is 23-139 g/L. The iodine containing composition can be autoradiographed when injected into blood vessels, and has a better embolization effect and stability.

17 Claims, 4 Drawing Sheets

Pre-dose            Post-dose

Pre-dose    Post-dose

Pre-dose    Post-dose

Pre-dose                Post-dose

Pre-dose                Post-dose

ETHANOL HARDENER AND USE THEREOF

CROSS-REFERENCE TO RELATED APPLICATIONS

The present application is a U.S. National Phase Application under 35 U.S.C. 371 of International Application No. PCT/CN2020/087705, filed on Apr. 29, 2020, which claims the benefit of Chinese Patent Application No. 201910355441.6 filed on Apr. 29, 2019. The entire disclosures of the above applications are incorporated herein by reference in their entirety.

TECHNICAL FIELD

The present invention relates to an ethanol-based sclerosing agent and use thereof.

BACKGROUND

Vascular malformations, also formerly known as hemangiomas, originate from tumors or malformations of the blood or lymphatic vessels. The pathogenesis of the vascular malformation is unknown at present. The clinical manifestations are various, and can be found in superficial tissues, deep tissues and even internal organs of the body. Previously, the therapy usually includes arterial ligation or surgical excision. However, such treatment has poor prognosis and high risks of relapse, deterioration and hemorrhage.

With the development of interventional radiology in recent years, sclerosing agents have become the first choice for treating vascular malformations. Sclerosing agents can effectively treat vascular malformations and varicosity. The action mechanism of sclerosing agents is to damage vascular endothelial cells through different ways, such that target blood vessels are sclerosed to produce fiber ropes which can be finally absorbed by surrounding tissues, so as to achieve the aims of relieving symptoms, improving appearance and alleviating hemodynamic disorders. Currently used sclerosing agents in clinical practice include ethanol, polidocanol, lauromacrogol, sodium myristyl sulfate, pingyangmycin and the like. Among these, the sclerosing effect of ethanol is obviously superior to those of other sclerosing agents.

Ethanol is a sclerosing agent with high infiltration. It denatures hemoglobin through dehydration and denudation and destroys vascular endothelial cells, rapidly causing focal tissue necrosis and thrombosis. This erosion effect is a mechanism of ethanol for treating vascular malformations. Ethanol has good therapeutic effect on both venous malformation and arteriovenous malformation. Especially for arteriovenous malformation, ethanol is the only clinically verified and effective sclerosing agent.

However, ethanol is also of a high risk of use due to its erosive nature. For example, its unfavorable entry into normal tissues such as nerves, muscles or connective tissue, especially into arteries, can result in irreversible necrosis in the normal tissue. Also, it is technically and empirically demanding for clinicians for using a sclerosing agent, and currently ethanol-based sclerosing agents are not approved for treatment of vascular malformations.

The above risks mainly come from the fact that ethanol cannot be traced after intravascular injection. To solve this problem, it has been reported in literature that a mixture of ethanol and iodized oil can be used for treating vascular malformation, and can be tracked after intravascular injection.

However, the above method still has the following problems:

a. Use of the mixture of ethanol/iodized oil will dilute ethanol, and thus reduce the angiosclerosis effect and the therapeutic effect;

b. The mixture solution is unstable, should be prepared right before use, and requires repeated extrusion and uniform mixing before use; otherwise, it will separate after a short time of standing;

c. The iodized oil and ethanol are incompatible, and may separate after the mixture solution is injected into a blood vessel, which may lead to an inaccurate tracing;

d. Iodized oil is insoluble in water and can be dispersed into small oil droplets after being injected into blood vessels, thus leading to risk of embolism.

Therefore, there is a need for developing an ethanol-based sclerosing agent with better safety and efficacy.

CONTENT OF THE PRESENT INVENTION

The present invention provides an ethanol-based sclerosing agent and use thereof, so as to overcome the defects that the drug effect of the ethanol-based sclerosing agent is unsatisfying and ethanol cannot be accurately traced in the prior art. The ethanol-based sclerosing agent disclosed herein enables an accurate tracing of ethanol, and has a good therapeutic effect on vascular malformations.

The present invention provides an iodine-containing composition, comprising ethanol, a water-soluble iodine preparation and water, wherein the volume percentage of ethanol is 76%-98% (i.e., the ratio of the volume of ethanol/the total volume of the iodine-containing composition); the mass-volume ratio of iodine in the water-soluble iodine preparation to the iodine-containing composition is 23-139 g/L.

In one embodiment, the iodine-containing composition can be an iodine-containing composition for use as a medicament.

In one embodiment, the iodine-containing composition can be an iodine-containing composition for treating vascular malformation.

In one embodiment, the iodine-containing composition can be an iodine-containing composition for use as an ethanol-based sclerosing agent.

In one embodiment, ethanol can be conventional ethanol in the art, such as ethanol for pharmaceutical injection.

In one embodiment, ethanol can be present in a volume percentage of 78%-95% (for example, 80%, 82%, 83%, 86%, or 90%), 78%-90% (for example, 80%; for another example, 83%; for still another example, 82%), and preferably 86%-90% (for example, 86%).

In the iodine-containing composition, the water-soluble iodine preparation refers to a conventional organic iodide in the art.

In one embodiment, the water-soluble iodine preparation can be one or more of iohexol, ioversol and iodixanol, and can also be iohexol.

In one embodiment, the mass-volume ratio of iodine in the water-soluble iodine preparation to the iodine-containing composition can be 35-121 g/L (for example, 46 g/L, 49 g/L, 70 g/L, 71 g/L or 93 g/L), or 46-121 g/L (for example, 49 g/L; for another example, 69 g/L; for still another example, 71 g/L; for still another example, 92 g/L).

In one embodiment, the mass-volume ratio of the water-soluble iodine preparation to the iodine-containing composition can be 50-300 g/L (for example, 75 g/L, 100 g/L, 150 g/L, 200 g/L, or 260 g/L), can further be 75-260 g/L (for example, 100 g/L), and can still further be 150-260 g/L (for example, 200 g/L).

In one embodiment, water can be conventional water for injection in the art, as long as it meets the pharmacopoeia regulations and complies with the specifications for pharmaceuticals.

In one embodiment, the iodine-containing composition can consist of ethanol, the water-soluble iodine preparation and water.

In one preferred embodiment of the present invention, the iodine-containing composition comprises the following amounts of ingredients per 1000 mL:

| | |
|---|---|
| ethanol | 760-980 mL |
| mass of iodine | 23-139 g |
| water for injection | the balance |

In one preferred embodiment of the present invention, the iodine-containing composition comprises the following amounts of ingredients per 1000 mL:

| | |
|---|---|
| ethanol | 760-980 mL |
| iohexol | 50-300 g |
| water for injection | the balance |

In one preferred embodiment of the present invention, the iodine-containing composition comprises the following amounts of ingredients per 1000 mL:

| | |
|---|---|
| ethanol | 800-900 mL |
| iohexol | 100-260 g |
| water for injection | the balance |

In one preferred embodiment of the present invention, the iodine-containing composition comprises the following amounts of ingredients per 1000 mL:

| | |
|---|---|
| ethanol | 820-900 mL |
| ioversol or iodixanol | 49-71 g |
| water for injection | the balance |

In one preferred embodiment of the present invention, the iodine-containing composition comprises the following amounts of ingredients per 1000 mL, wherein the mass of iodine in 1000 mL of the iodine-containing composition is 23-139 g:

| | |
|---|---|
| ethanol | 760-980 mL |
| iohexol | 50-300 g |
| water for injection | the balance |

In one preferred embodiment of the present invention, the iodine-containing composition comprises the following amounts of ingredients per 1000 mL, wherein the mass of iodine in 1000 mL of the iodine-containing composition is 46-119 g:

| | |
|---|---|
| ethanol | 800-900 mL |
| iohexol | 100-260 g |
| water for injection | the balance |

In one preferred embodiment of the present invention, the iodine-containing composition comprises the following amounts of ingredients per 1000 mL, wherein the mass of iodine in 1000 mL of the iodine-containing composition is 23-139 g:

| | |
|---|---|
| ethanol | 820-900 mL |
| water-soluble iodine preparation | 50-300 g |
| water for injection | the balance |

In one preferred embodiment of the present invention, the iodine-containing composition comprises the following amounts of ingredients per 1000 mL, wherein the mass of iodine in 1000 mL of the iodine-containing composition is 46-71 g:

| | |
|---|---|
| ethanol | 820-900 mL |
| water-soluble iodine preparation | 100-200 g |
| water for injection | the balance |

In one preferred embodiment of the present invention, the iodine-containing composition comprises amounts of ingredients per 1000 mL according to any of the following schemes:

scheme 1:

| | |
|---|---|
| ethanol | 830 ml |
| iohexol | 200 g |
| water for injection | the balance | scheme 2:

| | |
|---|---|
| ethanol | 820 ml |
| ioversol | 150 g |
| water for injection | the balance | scheme 3:

| | |
|---|---|
| ethanol | 900 ml |
| iodixanol | 100 g |
| water for injection | the balance | scheme 4:

| | |
|---|---|
| ethanol | 980 ml |
| iohexol | 50 g |
| water for injection | the balance | scheme 5:

| | |
|---|---|
| ethanol | 760 ml |
| iohexol | 300 g |
| water for injection | the balance | scheme 6:

| | |
|---|---|
| ethanol | 800 ml |
| iohexol | 260 g |
| water for injection | the balance | scheme 7:

| | |
|---|---|
| ethanol | 860 ml |
| iohexol | 150 g |
| water for injection | the balance | scheme 8:

| | |
|---|---|
| ethanol | 950 ml |
| iohexol | 50 g |
| water for injection | the balance | scheme 9:

| | |
|---|---|
| ethanol | 900 ml |
| iohexol | 100 g |
| water for injection | the balance | scheme 10:

| | |
|---|---|
| ethanol | 860 ml |
| iohexol | 75 g |
| water for injection | the balance | scheme 11:

| | |
|---|---|
| ethanol | 780 ml |
| iohexol | 150 g |
| water for injection | the balance |

The present invention also provides a method for preparing the iodine-containing composition described above, comprising: mixing the water-soluble iodine preparation, ethanol and water.

In one embodiment, the mixing can be implemented by stirring.

In one embodiment, the iodine-containing composition can be a transparent and clear solution.

In one embodiment, the iodine-containing composition can be sterilized at high temperature.

The method for high temperature sterilization can be a conventional method in the art. The temperature for high-temperature sterilization is preferably 115-121° C., for example, 121° C. The time for high-temperature sterilization is preferably 7-30 min, for example, 15 min.

In one embodiment, the iodine-containing composition can be contained in an ampoule.

The ampoule can be a conventional ampoule in the art, preferably a glass ampoule.

Further, the iodine-containing composition can be filled into several ampoules for preservation. The filling volume of the iodine-containing composition is not limited, preferably 5-15 mL.

The present invention also provides use of the iodine-containing composition described above as an ethanol-based sclerosing agent.

The present invention further provides use of the iodine-containing composition described above in preparing a medicament for treating vascular malformation. In the use, the iodine-containing composition can be used as an ethanol-based sclerosing agent.

The present invention further provides a method for treating vascular malformation, comprising administering to a patient a therapeutically effective amount of the iodine-containing composition described above.

In the treatment method, the patient can be a mammal, such as a mouse or a human.

In the treatment method, the iodine-containing composition can be administered by injection.

The present invention provides a pharmaceutical composition, comprising ethanol, a water-soluble iodine preparation and water for injection, wherein the volume percentage of ethanol is 76%-98%; the mass-volume ratio of the water-soluble iodine preparation to the composition is 50-300 g/L; the mass-volume ratio of iodine in the water-soluble iodine preparation to the composition is 23-139 g/L; the balance is water for injection.

In the pharmaceutical composition, ethanol can be conventional ethanol in the art, such as ethanol for pharmaceutical injection.

In the pharmaceutical composition, ethanol can be present in a volume percentage of 78%-90% (for example, 80%; for another example, 83%; for still another example, 82%), and preferably 86%-90% (for example, 86%).

In the pharmaceutical composition, the water-soluble iodine preparation refers to a conventional organic iodide in the art. The water-soluble iodine preparation can be one or more of iohexol, ioversol and iodixanol, and preferably iohexol.

In the pharmaceutical composition, the mass-volume ratio of the water-soluble iodine preparation to the pharmaceutical composition can be 75-260 g/L (for example, 100 g/L), and preferably 150-260 g/L (for example, 200 g/L).

In the pharmaceutical composition, the mass-volume ratio of iodine in the water-soluble iodine preparation to the iodine-containing composition can be 46-121 g/L (for example, 49 g/L; for another example, 69 g/L; for still another example, 71 g/L; for still another example, 92 g/L).

In the pharmaceutical composition, water for injection can be conventional water for injection in the art, as long as it meets the pharmacopoeia regulations and complies with the specifications for pharmaceuticals.

In one preferred embodiment of the present invention, the pharmaceutical composition comprises the following amounts of ingredients per 1000 mL, wherein the mass of iodine in 1000 mL of the pharmaceutical composition is 23-139 g:

| | |
|---|---|
| ethanol | 760-980 mL |
| iohexol | 50-300 g |
| water for injection | the balance |

In one preferred embodiment of the present invention, the pharmaceutical composition comprises the following amounts of ingredients per 1000 mL, wherein the mass of iodine in 1000 mL of the pharmaceutical composition is 46-119 g:

| | |
|---|---|
| ethanol | 800-900 mL |
| iohexol | 100-260 g |
| water for injection | the balance |

In one preferred embodiment of the present invention, the pharmaceutical composition comprises the following amounts of ingredients per 1000 mL, wherein the mass of iodine in 1000 mL of the pharmaceutical composition is 23-139 g:

| ethanol | 820-900 mL |
|---|---|
| water-soluble iodine preparation | 50-300 g |
| water for injection | the balance |

In one preferred embodiment of the present invention, the pharmaceutical composition comprises the following amounts of ingredients per 1000 mL, wherein the mass of iodine in 1000 mL of the pharmaceutical composition is 46-71 g:

| ethanol | 820-900 mL |
|---|---|
| water-soluble iodine preparation | 100-200 g |
| water for injection | the balance |

In one preferred embodiment of the present invention, the pharmaceutical composition comprises ethanol, the water-soluble iodine preparation and water for injection, wherein the volume percentage of ethanol is 76%-98%; the mass-volume ratio of the water-soluble iodine preparation to the composition is 50-300 g/L; the mass-volume ratio of iodine in the water-soluble iodine preparation to the composition is 23-139 g/L; the balance is water for injection.

The present invention further provides a method for preparing the pharmaceutical composition, comprising:
mixing and stirring the water-soluble iodine preparation, ethanol and water for injection to obtain a transparent and clear solution, filling into ampoules, sealing, and sterilizing at high temperature.

The method for high temperature sterilization can be a conventional method in the art. The temperature for high-temperature sterilization is preferably 115-121° C., for example, 121° C. The time for high-temperature sterilization is preferably 7-30 min, for example, 15 min.

The ampoule can be a conventional ampoule in the art, preferably a glass ampoule.

Further, the pharmaceutical composition can be filled into several ampoules for preservation. The filling volume of the pharmaceutical composition is not limited, preferably 5-15 mL.

The pharmaceutical composition is used as an ethanol-based sclerosing agent.

The present invention also provides use of the pharmaceutical composition as an ethanol-based sclerosing agent in preparing a medicament for treating vascular malformation.

As used herein, "room temperature" refers to 10-30° C.

The above preferred conditions may be combined arbitrarily to obtain preferred embodiments of the present invention without departing from the general knowledge in the art.

The reagents and starting materials used in the present invention are commercially available.

Compared with the prior art, the pharmaceutical composition has the following beneficial effects as an ethanol-based sclerosing agent:

1. The ethanol-based sclerosing agent disclosed herein can facilitate autoradiography when administered intravascularly, so as to avoid irreversible damages due to unfavorable exposure to normal tissues such as nerves, muscles or connective tissues, especially to arteries;
2. Compared with an ethanol/iodized oil mixture, the ethanol-based sclerosing agent disclosed herein is more stable and can avoid the risk of thrombosis posed by iodized oil when administered intravascularly;
3. The ethanol-based sclerosing agent disclosed herein has a good angiosclerosis effect, and its embolization efficiency is greater than 65% and up to 100%.

DETAILED DESCRIPTION OF THE PREFERRED EMBODIMENT

Figure 1:
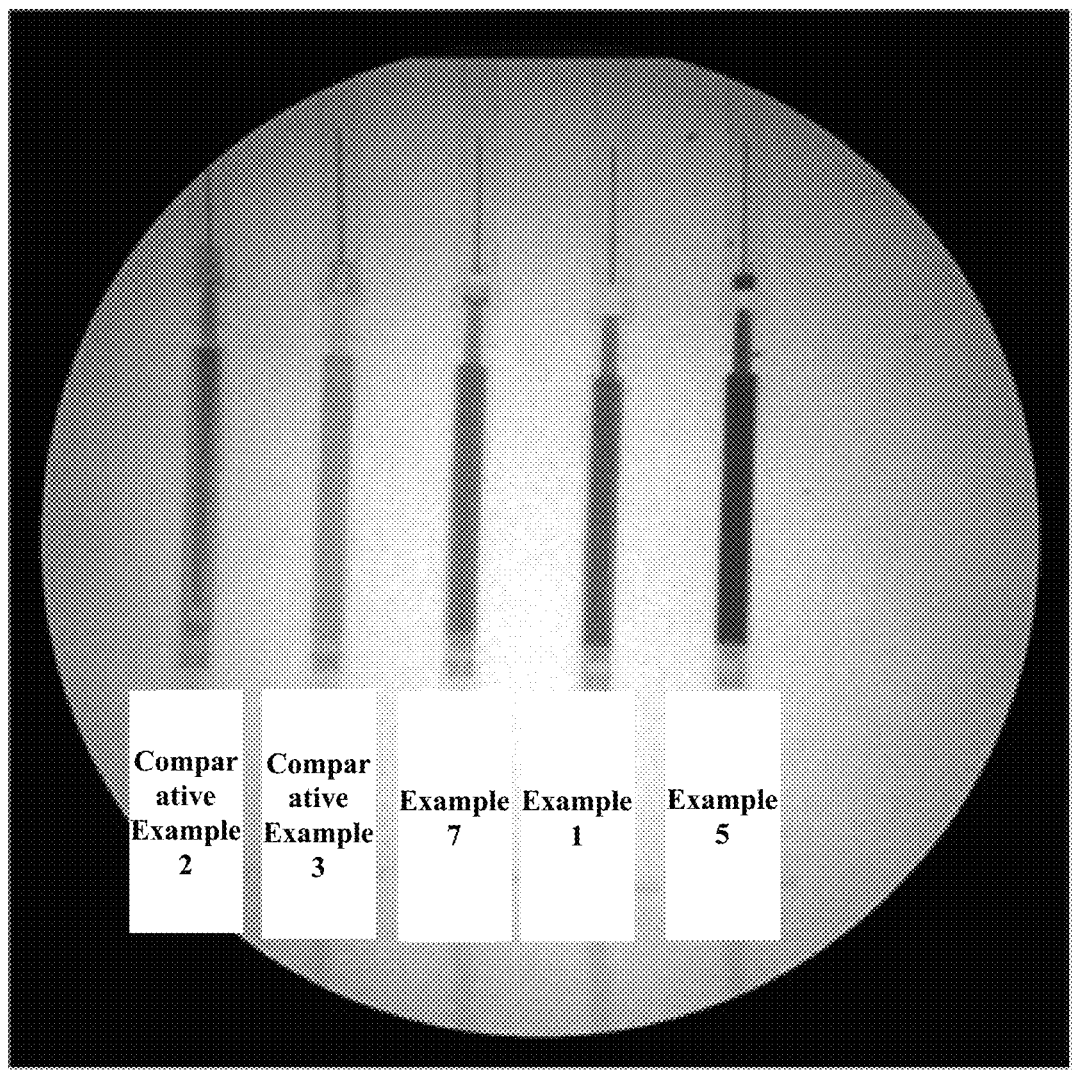
FIG. 1 is a radiograph showing the in-vitro enhancing effect of the sclerosing agents prepared in Examples 1, 5 and 7 and Comparative Examples 2 and 3.

The present invention is further illustrated by the following examples, which are not intended to limit the present invention. Experimental procedures without specified conditions in the following examples were performed in accordance with conventional procedures and conditions, or in accordance with instructions.

In the following examples, iohexol and ioversol were purchased from Zhejiang Starry Pharmaceutical Co., Ltd.; iodixanol was purchased from Lianyungang Runzhong Pharmaceutical Co., Ltd.; ethanol was purchased from Hunan Jiudian Pharmaceutical Co., Ltd.; water for injection was purchased from Thermofisher; iodized oil injection was purchased from Yantai Luyin Pharmaceutical Co., Ltd., with a specification of 10 mL, an iodine content of 37%-41% (w/w; taking the median 39%) and a density of about 1.355 g/mL.

EXAMPLE 1

The sclerosing agent comprised the following amounts of ingredients per 1000 mL, wherein the mass of iodine in 1000 mL of the sclerosing agent was 93 g:

| ethanol | 830 ml |
|---|---|
| iohexol | 200 g |
| water for injection | the balance |

Preparation: 200 g of iohexol was added into ethanol, and the mixture was continuously stirred to mix well. The balance of water for injection was slowly added to obtain a transparent and clear solution. Glass ampoules were filled with the solution, sealed, and sterilized at a high temperature of 121° C. for 15 minutes to obtain the agent.

EXAMPLE 2

The sclerosing agent comprised the following amounts of ingredients per 1000 mL, wherein the mass of iodine in 1000 mL of the sclerosing agent was 71 g:

| ethanol | 820 ml |
| ioversol | 150 g |
| water for injection | the balance |

The preparation method referred to that in Example 1.

EXAMPLE 3

The sclerosing agent comprised the following amounts of ingredients per 1000 mL, wherein the mass of iodine in 1000 mL of the sclerosing agent was 49 g:

| ethanol | 900 ml |
| iodixanol | 100 g |
| water for injection | the balance |

The preparation method referred to that in Example 1.

EXAMPLE 4

The sclerosing agent comprised the following amounts of ingredients per 1000 mL, wherein the mass of iodine in 1000 mL of the sclerosing agent was 23 g:

| ethanol | 980 ml |
| iohexol | 50 g |
| water for injection | the balance |

The preparation method referred to that in Example 1.

EXAMPLE 5

The sclerosing agent comprised the following amounts of ingredients per 1000 mL, wherein the mass of iodine in 1000 mL of the sclerosing agent was 139 g:

| ethanol | 760 ml |
| iohexol | 300 g |
| water for injection | the balance |

The preparation method referred to that in Example 1.

EXAMPLE 6

The sclerosing agent comprised the following amounts of ingredients per 1000 mL, wherein the mass of iodine in 1000 mL of the sclerosing agent was 121 g:

| ethanol | 800 ml |
| iohexol | 260 g |
| water for injection | the balance |

The preparation method referred to that in Example 1.

EXAMPLE 7

The sclerosing agent comprised the following amounts of ingredients per 1000 mL, wherein the mass of iodine in 1000 mL of the sclerosing agent was 70 g:

| ethanol | 860 ml |
| iohexol | 150 g |
| water for injection | the balance |

The preparation method referred to that in Example 1.

EXAMPLE 8

The sclerosing agent comprised the following amounts of ingredients per 1000 mL, wherein the mass of iodine in 1000 mL of the sclerosing agent was 23 g:

| ethanol | 950 ml |
| iohexol | 50 g |
| water for injection | the balance |

The preparation method referred to that in Example 1.

EXAMPLE 9

The sclerosing agent comprised the following amounts of ingredients per 1000 mL, wherein the mass of iodine in 1000 mL of the sclerosing agent was 46 g:

| ethanol | 900 ml |
| iohexol | 100 g |
| water for injection | the balance |

The preparation method referred to that in Example 1.

EXAMPLE 10

The sclerosing agent comprised the following amounts of ingredients per 1000 mL, wherein the mass of iodine in 1000 mL of the sclerosing agent was 35 g:

| ethanol | 860ml |
| iohexol | 75 g |
| water for injection | the balance |

The preparation method referred to that in Example 1.

EXAMPLE 11

The sclerosing agent comprised the following amounts of ingredients per 1000 mL, wherein the mass of iodine in 1000 mL of the sclerosing agent was 70 g:

| ethanol | 780 ml |
| iohexol | 150 g |
| water for injection | the balance |

The preparation method referred to that in Example 1.

Comparative Example 1

The sclerosing agent comprised the following amounts of ingredients per 1000 mL, wherein the mass of iodine in 1000 mL of the sclerosing agent was 162 g:

| | |
|---|---|
| ethanol | 700 ml |
| iohexol | 350 g |
| water for injection | the balance |

The preparation method referred to that in Example 1.

Comparative Example 2

The sclerosing agent comprised the following amounts of ingredients per 6 mL, without water for injection, wherein the mass of iodine in 6 mL of the sclerosing agent was 1.355 g:

| | |
|---|---|
| ethanol | 5 ml |
| iodized oil injection | 1 ml |

Preparation: Absolute ethanol and iodized oil were mixed at a ratio of 5:1, and the mixture was shaken to mix well; alternatively, anhydrous ethanol and iodized oil were mixed into an emulsion using two syringes connected to a three-way connector. The agent was prepared right before use.

Comparative Example 3

The sclerosing agent comprised the following amounts of ingredients per 1000 mL, wherein the mass of iodine in 1000 mL of the sclerosing agent was 14 g:

| | |
|---|---|
| ethanol | 950 ml |
| iohexol | 30 g |
| water for injection | the balance |

The preparation method referred to that in Example 1.

Comparative Example 4

The sclerosing agent comprised the following amounts of ingredients per 1000 mL, wherein the mass of iodine in 1000 mL of the sclerosing agent was 162 g:

| | |
|---|---|
| ethanol | 760 ml |
| iohexol | 350 g |
| water for injection | the balance |

The preparation method referred to that in Example 1.

Effect Example 1 Tests of Imaging Effect 1.1 Test of In-Vitro Imaging Effect

Figure 2:
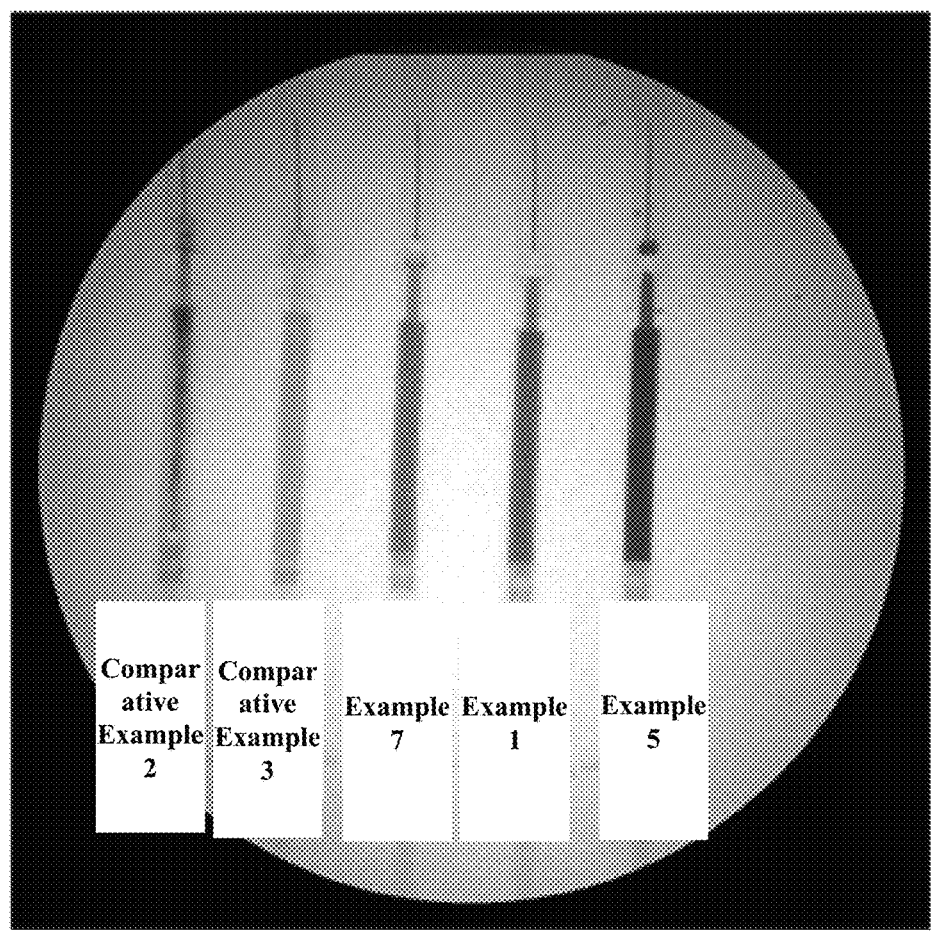
FIG. 2 is a radiograph showing the in-vitro enhancing effect of the sclerosing agents prepared in Examples 1, 5 and 7 and Comparative Examples 2 and 3 after being left standing for 3 min.

The agents of Example 1 (containing 200 g of iohexol and 93 g of iodine per 1000 mL), Example 5 (containing 300 g of iohexol and 139 g of iodine per 1000 mL), Example 7 (containing 150 g of iohexol and 70 g of iodine per 1000 mL), Comparative Example 2 (containing 167 mL of iodized oil injection and 225.8 g of iodine per 1000 mL) and Comparative Example 3 (containing 30 g of iohexol and 14 g of iodine per 1000 mL) were loaded into syringes and tested under X-ray (C-shaped arm) for the in-vitro imaging effect; the agent of Comparative Example 2 was prepared right before use. The in-vitro imaging effect is shown in FIG. 1. After the sclerosing agents were left standing for 3 minutes, the in-vitro enhancing effect was observed under X-ray (C-shaped arm), as shown in FIG. 2.

In FIG. 1, the agents of Example 7, Example 5 and Example 1 showed significantly stronger effect than Comparative Example 2, while for Comparative Example 2, a non-uniform effect was observed immediately after preparation. More severe condition was observed after only 3 minutes of standing, as shown in FIG. 2. More oil droplets of large particle size were observed to be separated from ethanol. This indicates that the agent of Comparative Example 2 may have compromised in-vivo enhancing effect and safety. The agent of Comparative Example 3 showed weak enhancing effect and was incapable of providing sufficient enhancing effect for tracing in-vivo.

1.2 Test of In-Vivo Enhancing Effect

Figure 3:
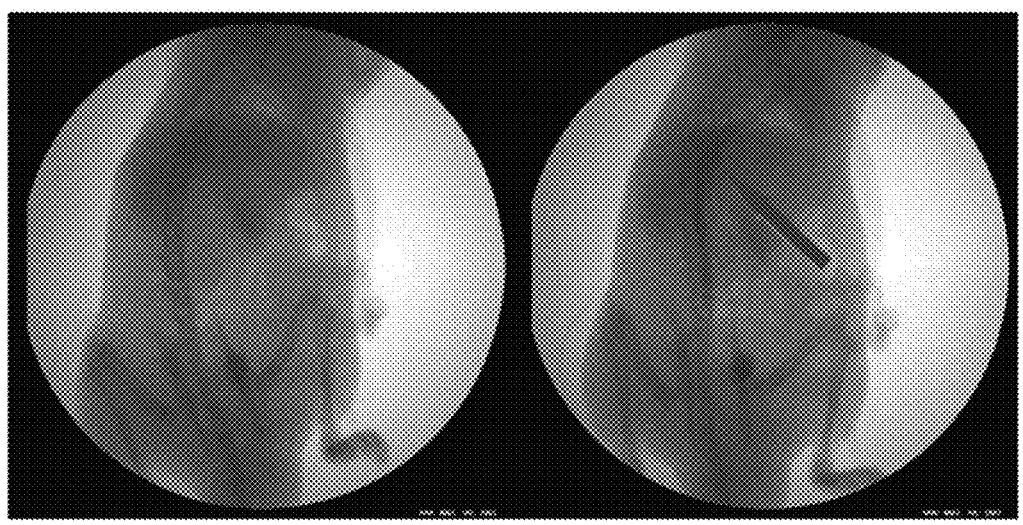
FIG. 3 is a radiograph showing the in-vivo enhancing effect in a rat of the sclerosing agent prepared in Example 1.
Figure 4:
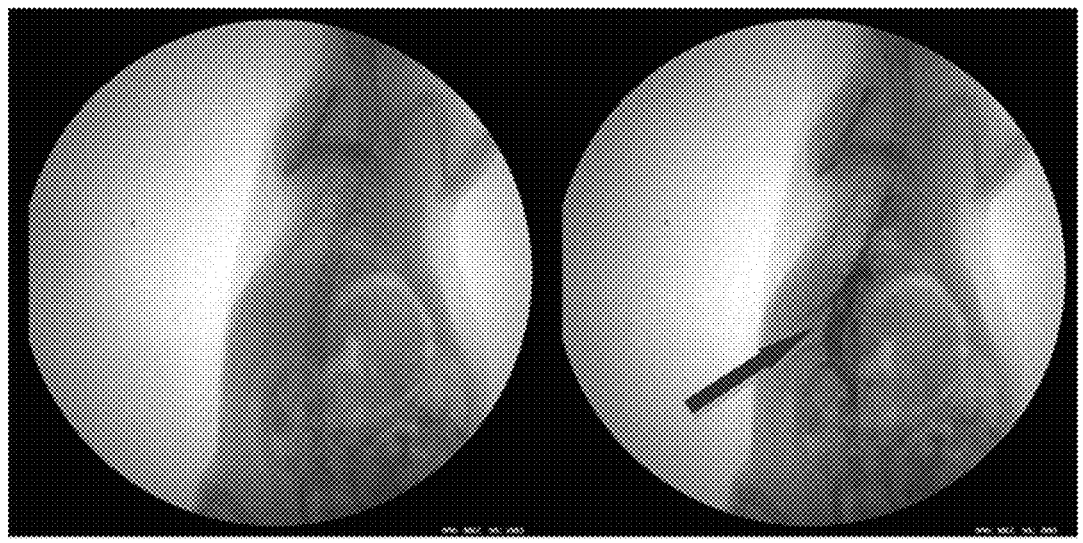
FIG. 4 is a radiograph showing the in-vivo enhancing effect in a rat of the sclerosing agent prepared in Example 5.
Figure 5:
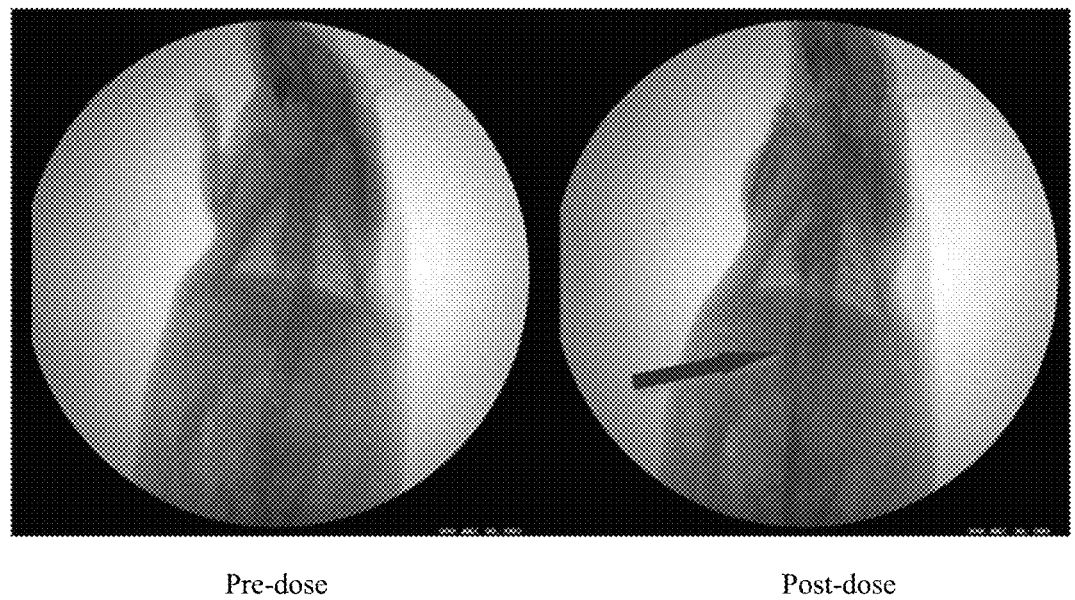
FIG. 5 is a radiograph showing the in-vivo enhancing effect in a rat of the sclerosing agent prepared in Example 7.
Figure 6:
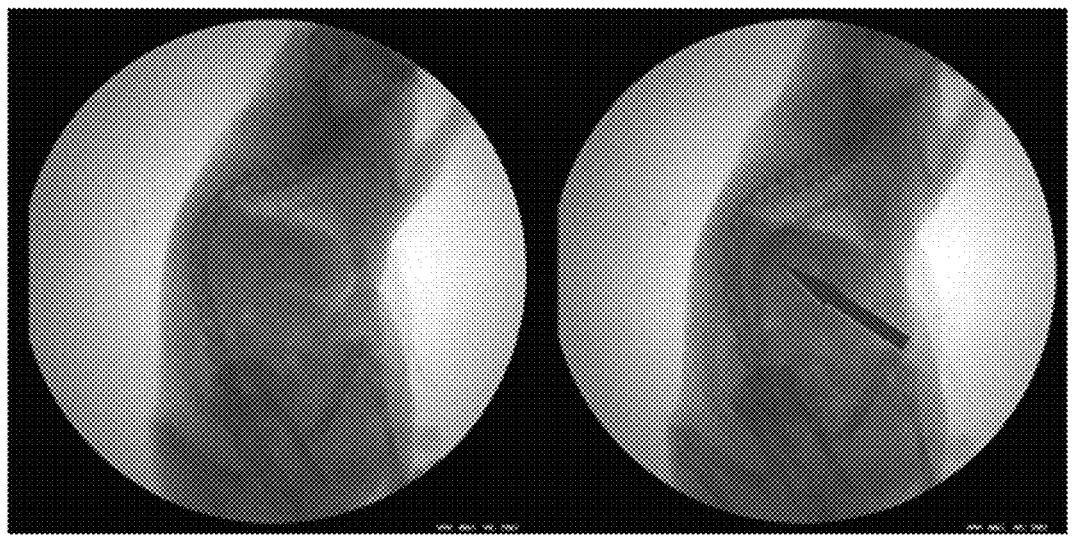
FIG. 6 is a radiograph showing the in-vivo enhancing effect in a rat of the sclerosing agent prepared in Comparative Example 2.
Figure 7:
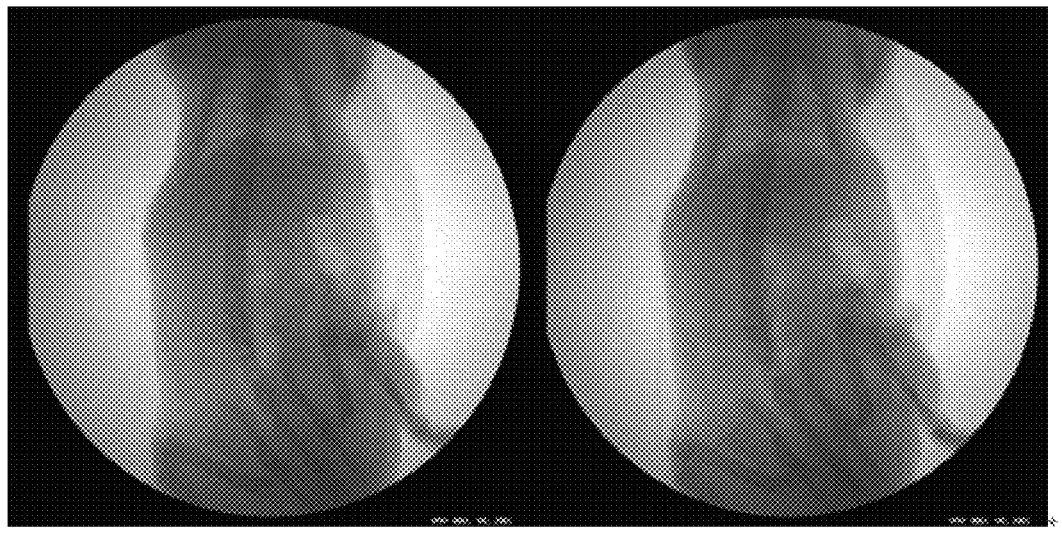
FIG. 7 is a radiograph showing the in-vivo enhancing effect in a rat of the sclerosing agent prepared in Comparative Example 3.

Male SD rats were selected for the test. After anesthesia by sodium pentobarbital, the rats were administered with the agents of Example 1 (containing 200 g of iohexol and 93 g of iodine per 1000 mL), Example 5 (containing 300 g of iohexol and 139 g of iodine per 1000 mL), Example 7 (containing 150 g of iohexol and 70 g of iodine per 1000 mL), Comparative Example 2 (containing 167 mL of iodized oil injection and 225.8 g of iodine per 1000 mL) and Comparative Example 3 (containing 30 g of iohexol and 14 g of iodine per 1000 mL) by injection via inferior vena cava to test the in-vivo enhancing effect of the agents, as shown in FIGS. 3-7. The enhancing effect of Example 1 is shown in FIG. 3. The enhancing effect of Example 5 is shown in FIG. 4. The enhancing effect of Example 6 is shown in FIG. 5. The enhancing effect of Comparative Example 2 is shown in FIG. 6. The enhancing effect of Comparative Example 3 is shown in FIG. 7. The results showed that Example 7 had similar enhancing effect to Comparative Example 2, Examples 5 and 1 had significantly stronger effect than Comparative Example 2, and no significant enhancing effect was observed for Comparative Example 3.

It can be seen from the test results of in-vivo and in-vitro enhancing effect that the sclerosing agent of Comparative Example 3 has no significant enhancing effect in vivo and cannot function to trace ethanol; the enhancing effects of Examples 5 and 1 are significantly stronger than that of Comparative Example 2, and Example 7 is similar to Comparative Example 2 in enhancing effect. However, the sclerosing agent prepared in Comparative Example 2 is extremely unstable in system. It separates in a short term into iodized oil and ethanol, and should be prepared right before administration, which is inconvenient for clinical use. In addition, the unstable system also brings great risks in safety, including compromised tracing effect of the preparation and formation of embolism due to iodized oil droplets in circulation.

Effect Example 2 Viscosity Test

The viscosity of Examples 1, 5 and 7 and ethanol was measured by a capillary viscometer at an ambient temperature of 20° C. The capillary diameter was 0.5-0.6 mm and the viscometer constant was 0.005085 $mm^2/s^2$. The time difference of liquid passing through the capillary was recorded. See Table 1 for details.

Viscosity=time difference×viscometer constant

TABLE 1

| Group | Time difference (s) | Viscosity ($mm^2/s$) |
|---|---|---|
| Example 1 (20% iohexol) | 582 | 2.96 |
| Example 5 (30% iohexol) | 863 | 4.39 |

TABLE 1-continued

| Group | Time difference (s) | Viscosity (mm$^2$/s) |
|---|---|---|
| Example 7 (15% iohexol) | 496 | 2.52 |
| Ethanol | 245 | 1.25 |

The test results show that the preparations of the present invention significantly improve the viscosity of the ethanol-based sclerosing agent and can be beneficial to improving the enhancing effect.

Effect Example 3 Embolic Effect in Rabbit Ear Vein

Sixty healthy male rabbits with body weight of 2.5±0.2 kg were selected and divided into 6 groups of 10. The rabbits were anesthetized with a 3% sodium pentobarbital solution by intraperitoneal injection at 0.8 mL/kg. An anticoagulated and disinfected PE-8 catheter (0.20 mm×0.36 mm) was inserted into the distal end of the ear vein, until the end of the catheter reached the midpoint of the ear vein. The in-vitro end of the catheter was connected with a 1-mL syringe through a cannula.

0.1 mL of each of the sclerosing agents of various embodiments with different components was injected at a constant speed through the PE-8 catheter. After 30 seconds, the catheter was slowly and gently withdrawn, and a cotton pad was used for hemostasis. Both left and right ears of the animals were treated with the same procedures. The animals after sclerosing treatment were accommodate in individual cages. After a one-month recovery period, after visual inspection, a normal saline containing India ink was slowly injected at the distal end of the ear vein, so as to observe and record whether the blood vessels were completely embolized. The embolization ratio in each group was recorded (Table 2).

TABLE 2

Embolic effect of sclerosing agents with different components in rabbit ear vein

| Group | Volume of ethanol per 1000 mL (mL) | Mass of iohexol per 1000 mL (g) | Ratio of completely embolized vessels |
|---|---|---|---|
| Example 1 | 830 | 200 | 100% (20/20)** |
| Example 2 | 820 | 150 | 90% (18120)* |
| Example 3 | 900 | 100 | 85% (17120)* |
| Example 4 | 980 | 50 | 85% (17120)* |
| Example 5 | 760 | 300 | 85% (17120)* |
| Example 6 | 800 | 260 | 85% (17/20)* |
| Example 7 | 860 | 150 | 95% (19120)** |
| Example 8 | 950 | 50 | 65% (13/20) |
| Example 9 | 900 | 100 | 90% (18/20)* |
| Example 10 | 860 | 75 | 85% (17/20)* |
| Example 11 | 780 | 150 | 80% (16/20) |
| Comparative Example 1 | 700 | 350 | 25% (5/20)* |
| Comparative Example 2 | 833 | 167 mL of iodized oil | 45% (9/20) |
| Comparative Example 3 | 950 | 30 | 60% (12/20) |
| Control group (absolute ethanol) | 1000 | 0 | 60% (12/20) |

Notes:
in Table 2, "*" denotes p < 0.05; "**" indicates p < 0.01 vs. absolute ethanol, Chi-square fisher's exact test.

The results showed that the vascular embolization ratios of Examples 1, 5, 7, 4, 6, 9 and 10 were all greater than 85% and were significantly higher than that of the absolute ethanol group (p<0.05), and the vascular embolization ratios of Examples 8 and 11 were greater than 65% and were higher than that of the absolute ethanol group. The vascular embolization ratios of Comparative Examples 1 and 2 were only 25% and 45%, respectively, significantly lower than those of the compositions of the present invention; the vascular embolic effect of Comparative Example 3 was similar to that of absolute ethanol, and was also significantly lower than those of the compositions of the present invention.

Ethanol works as an angiosclerosis agent by destroying blood vessels through its strong dehydration and denudation effects, and it is generally believed that a higher concentration gives a better sclerosing effect. However, ethanol has high mobility in blood vessels and a short time for actually acting on lesions, such that more ethanol is required to ensure the therapeutic effect for treating vascular malformation, thus inevitably increasing the safety risk.

The compositions of the present invention, when injected into blood vessels, not only facilitate autoradiography in blood vessels to avoid irreversible damage caused by unfavorable entry into normal tissues, but also have a surprising sclerosing and embolic effect stronger than that of absolute ethanol on the blood vessels. In addition, at present, no document has reported that water-soluble iodine preparations have a therapeutic effect on vascular malformations. In the test process, the inventor did not find any therapeutic effect on vascular malformations of any individual water-soluble iodine preparation.

Therefore, the water-soluble iodine preparation of a specific content and ethanol of a specific content in the composition work together to provide the synergistic effect.

For the synergistic effect, the inventor supposed that the composition achieves a proper viscosity due to the water-soluble iodine with a specific content in the formulation, such that the composition can stay at the lesions for a certain time to produce a sufficient sclerosing and damaging effect on the lesions, thus generating a significantly improved embolic effect and no other side effect.

The poor embolic effect of Comparative Example 1 may be attributed to the low ethanol concentration, which impairs its sclerosing effect.

For the weak embolic effect of Comparative Example 2, it is presumed that the following two reasons may be possible: the iodine oil dilutes the concentration of ethanol; the iodized oil and ethanol are mutually incompatible and are separated after administration into blood vessels, and the iodized oil is easy to deposit and attach on vascular endothelium because the density and the viscosity of the iodized oil are higher than those of the ethanol, and as such, the iodized oil blocks the sclerosing effect of ethanol on the lesions by direct contact, rather than prolongs the retention time of ethanol.

The weak embolic effect of Comparative Example 3 is attributed to the low concentration of the water-soluble iodine preparation, which reduces the retention time and impairs the sclerosing effect.

Therefore, the sclerosing agent of the present invention not only realizes the effect of accurately tracing ethanol, but also significantly improves the angiosclerosis effect.

Effect Example 4 Stability Test

The sclerosing agents prepared in some examples of the present invention and Comparative Example 4 were selected for accelerated stability test. The sclerosing agents were preserved for 6 months under the conditions of 40±2° C. and 75±5% humidity, and samples were taken for content assay before and after sterilization and at 1, 2, 3 and 6 months. The results of the sclerosing agents prepared in some examples of the present invention are detailed in Tables 3 and 4. For the sclerosing agent of Comparative Example 4, a small amount of iohexol precipitate was found in the solution after several hours of standing. The "labeled amounts" in Tables 3 and 4 refer to the specified amount of the active ingredient in a unit dose form.

The methods for content assay of iohexol and ethanol can be found in the *Chinese Pharmacopoeia*, 2015 edition.

TABLE 3

Iohexol content in percent of labeled amount

| Group | Before sterilization | After sterilization | 1 month | 2 months | 3 months | 6 months |
|---|---|---|---|---|---|---|
| Example 1 | 98.9% | 98.7% | 98.2% | 98.1% | 97.8% | 97.1% |
| Example 4 | 99.8% | 99.8% | 99.5% | 99.4% | 98.7% | 98.8% |
| Example 5 | 100.3% | 99.8% | 99.9% | 99.7% | 99.1% | 98.7% |
| Example 6 | 101.2% | 101.2% | 100.7% | 100.4% | 99.8% | 100.0% |
| Example 7 | 99.4% | 99.5% | 99.3% | 98.9% | 98.7% | 98.0% |
| Example 8 | 100.9% | 100.4% | 100.5% | 100.1% | 99.8% | 99.2% |

TABLE 4

Ethanol content in percent of labeled amount

| Group | Before sterilization | After sterilization | 1 month | 2 months | 3 months | 6 months |
|---|---|---|---|---|---|---|
| Example 1 | 100.2% | 100.0% | 99.7% | 99.4% | 99.1% | 98.7% |
| Example 4 | 99.5% | 99.1% | 99.0% | 98.5% | 98.2% | 98.0% |
| Example 5 | 98.6% | 98.2% | 98.0% | 97.2% | 97.1% | 96.8% |
| Example 6 | 99.2% | 99.2% | 99.0% | 98.7% | 98.5% | 98.0% |
| Example 7 | 100.2% | 99.7% | 99.5% | 99.4% | 99.1% | 98.6% |
| Example 8 | 100.1% | 99.9% | 99.4% | 99.2% | 99.1% | 98.5% |

As can be seen from the above Tables 3 and 4, the stability data of the components suggest that the sclerosing agents of the present invention had a content within a predetermined range in the accelerated stability test and have good stability. In contrast, the composition prepared in Comparative Example 4 (the content of the water-soluble iodine preparation exceeds the range of the present application) cannot be preserved for a long period of time because a small amount of the water-soluble iodine preparation precipitate was found after several hours of standing.

What is claimed is:

1. An iodine-containing composition comprising: ethanol, a water-soluble iodine preparation and water,
    wherein the volume percentage of ethanol is 83-86%; the mass-volume ratio of iodine in the water-soluble iodine preparation to the iodine-containing composition is 70-93 g/L; and wherein the water-soluble iodine preparation is iohexol.

2. The iodine-containing composition according to claim 1, wherein the iodine-containing composition is a pharmaceutical composition comprising ethanol, a water-soluble iodine preparation and water for injection, and wherein the mass-volume ratio of the water-soluble iodine preparation to the iodine-containing composition is 150-200 g/L.

3. The iodine-containing composition according to claim 2, wherein
    the iodine-containing composition consists of ethanol, the water-soluble iodine preparation and water for injection.

4. The iodine-containing composition according to claim 1, wherein the iodine-containing composition satisfies one or more of the following conditions:
    ethanol is ethanol for pharmaceutical injection;
    the mass-volume ratio of the water-soluble iodine preparation to the iodine-containing composition is 150-200 g/L;
    water is water for injection; and
    the iodine-containing composition consists of ethanol, the water-soluble iodine preparation and water.

5. The iodine-containing composition according to claim 1, comprising amounts of ingredients per 1000 ml according to either of the following schemes:

| scheme 1: | |
|---|---|
| ethanol | 830 ml |
| iohexol | 200 g |
| water for injection | the balance |

| scheme 7: | |
|---|---|
| ethanol | 860 ml |
| iohexol | 150 g |
| water for injection | the balance |

6. The iodine-containing composition according to claim 1, wherein,
the mass-volume ratio of the water-soluble iodine preparation to the iodine-containing composition is 150 g/L or 200 g/L; and
the mass-volume ratio of iodine in the water-soluble iodine preparation to the iodine-containing composition is 70 g/L or 93 g/L.

7. The iodine-containing composition according to claim 1, wherein the iodine-containing composition is prepared by: mixing the water-soluble iodine preparation, ethanol and water to form the iodine-containing composition; and sterilizing the iodine-containing composition at 115-121° C.

8. The iodine-containing composition according to claim 1, wherein,
the mass-volume ratio of the water-soluble iodine preparation to the iodine-containing composition is 150 g/L or 200 g/L;
the mass-volume ratio of iodine in the water-soluble iodine preparation to the iodine-containing composition is 70 g/L or 93 g/L; and
wherein the iodine-containing composition is prepared by mixing the water-soluble iodine preparation, ethanol and water and sterilizing the iodine-containing composition at 115-121° C.

9. An iodine-containing composition according to claim 1, wherein
the iodine-containing composition consists of ethanol, the water-soluble iodine preparation and water; the mass-volume ratio of the water-soluble iodine preparation to the iodine-containing composition is 150 g/L or 200 g/L; the mass-volume ratio of iodine in the water-soluble iodine preparation to the iodine-containing composition is 70 g/L or 93 g/L;
wherein the iodine-containing composition is prepared by a method comprising the following steps: mixing and stirring the water-soluble iodine preparation, ethanol and water for injection to obtain a transparent and clear solution, filling the solution into ampoules, sealing the ampoules, and sterilizing the iodine-containing composition filled into the ampoules at 115-121° C.

10. A medicament, which comprises the iodine-containing composition according to claim 1.

11. A method for treating vascular malformation in a subject in need thereof, comprising administering an effective amount of the medicament according to claim 10.

12. An ethanol-based sclerosing agent, which comprises the iodine-containing composition according to claim 1.

13. A method of preparing the iodine-containing composition according to claim 1, comprising: mixing the water-soluble iodine preparation, ethanol and water; wherein the method satisfies one or more of the following conditions:
the mixing is implemented by stirring;
the iodine-containing composition is a transparent and clear solution;
the iodine-containing composition is sterilized at 115-121° C.; and
the iodine-containing composition is contained in an ampoule.

14. A method of treating vascular malformation, comprising: administering to a patient a therapeutically effective amount of the iodine-containing composition according to claim 1; wherein the method satisfies either one or both of the following conditions:
the patient is a mammal; and
the iodine-containing composition is administered by injection.

15. The method according to claim 14, wherein the patient is a mouse or a human.

16. A method for preparing an iodine-containing composition comprising the following steps: mixing and stirring a water-soluble iodine preparation, ethanol and water for injection to obtain a transparent and clear solution, filling the solution into ampoules, sealing the ampoules, and sterilizing the iodine-containing composition filled into the ampoules at 115-121° C.
wherein the iodine-containing composition consists of ethanol, the water-soluble iodine preparation and water; wherein the volume percentage of ethanol is 83%-86%; the mass-volume ratio of the water-soluble iodine preparation to the iodine-containing composition is 150 g/L or 200 g/L; the mass-volume ratio of iodine in the water-soluble iodine preparation to the iodine-containing composition is 70 or 93 g/L; and wherein the water-soluble
iodine preparation is iohexol.

17. A method for treating vascular malformation in a subject in need thereof, comprising administering an effective amount of an iodine-containing composition wherein the iodine-containing composition consists of ethanol, the water-soluble iodine preparation and water; wherein the volume percentage of ethanol is 83%-86%; the mass-volume ratio of the water-soluble iodine preparation to the iodine-containing composition is 150 g/L or 200 g/L; the mass-volume ratio of iodine in the water-soluble iodine preparation to the iodine-containing composition is 70 or 93 g/L; and wherein the water-soluble
iodine preparation is iohexol.

* * * * *